United States Patent [19]

Hider et al.

[11] Patent Number: 4,587,240

[45] Date of Patent: May 6, 1986

[54] PHARMACEUTICAL COMPOSITIONS

[75] Inventors: Robert C. Hider, Clacton; George Kontoghiorghes; Jack Silver, both of London; Michael A. Stockham, Saffron Walden, all of England

[73] Assignee: National Research Development Corp., London, England

[21] Appl. No.: 651,772

[22] Filed: Sep. 18, 1984

[30] Foreign Application Priority Data

Sep. 23, 1983 [GB] United Kingdom ............... 8325496

[51] Int. Cl.$^4$ .................. C07D 213/69; A61K 31/555
[52] U.S. Cl. ...................................... 514/188; 424/10; 424/147; 514/348; 546/296; 546/2; 546/6
[58] Field of Search ......................... 424/147, 295, 10; 546/296, 2, 6; 514/188, 348

[56] References Cited

U.S. PATENT DOCUMENTS

| | | | |
|---|---|---|---|
| 2,748,142 | 5/1956 | Clauson-Kaas et al. | 546/296 |
| 3,269,904 | 8/1966 | Bernstein et al. | 514/345 |
| 3,705,943 | 12/1972 | Kaufman | 514/188 |
| 3,968,118 | 7/1976 | Lohaus et al. | 546/296 |

FOREIGN PATENT DOCUMENTS

| | | | |
|---|---|---|---|
| 0105053A | 11/1984 | European Pat. Off. | |
| 42-23195 | 11/1967 | Japan . | |
| 53-98972 | 8/1978 | Japan | 546/296 |
| 58-32812 | 2/1983 | Japan . | |
| 790584 | 2/1958 | United Kingdom . | |
| 791719 | 3/1958 | United Kingdom . | |
| 1238106 | 7/1971 | United Kingdom . | |
| 1416397 | 12/1975 | United Kingdom . | |
| 2118176 | 10/1983 | United Kingdom | 546/296 |

OTHER PUBLICATIONS

Chemical Abstracts, 1968, vol. 69, No. 35956t (Japan 67-23351), Aug. 26, 1968.
Chemical Abstracts, 1968, vol. 69, No. 35967x (Japan 67-23194), Aug. 26, 1968.
Chemical Abstracts, 1968, vol. 69, No. 35968y (Japan 67-23196), Aug. 26, 1968.
Chemical Abstracts, 1970, vol. 72, No. 12596y (Japan 69-25582), Jan. 19, 1970.
Chemical Abstracts, 1970, vol. 72, No. 132534y (Japan 70-06268), Jan. 26, 1970.
Chemical Abstracts, 1970, vol. 72, No. 132537b (Japan 70-06267), Jan. 26, 1970.
Mizukami et al and Nishimura et al, Annual Reports of the Shionogi Research Laboratories, 1966, vol. 16, pp. 29 to 36 and 37 to 40.
Shaw et al, Journal of the American Chemical Society, 1949, vol. 71, pp. 67 to 70 and 70 to 73.
Landers et al, Inorganica Chimica Acta, 1981, vol. 51, pp. 109 to 115.
Hubbard et al, Inorganic Nuclear Chemical Letters, 1979, vol. 15, pp. 255 to 258.
Pitt et al, Development of Iron Chelators for Clinical Use, Anderson and Hiller (Editors), 1975, p. 137.

Primary Examiner—Ronald W. Griffin
Attorney, Agent, or Firm—Oblon, Fisher, Spivak, McClelland & Maier

[57] ABSTRACT

Compounds which are a 1-hydroxypyrid-2-one in which one or more of the hydrogen atoms attached to ring carbon atoms are replaced by a substituent selected from aliphatic acyl, aliphatic amide, aliphatic amine, carboxy, cyano, aliphatic ester, halogen, hydroxy and sulpho groups, alkoxy groups and alkoxy groups substituted by an alkoxy, aliphatic amide, aliphatic amine, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms in the compound is effected only by substituents selected from aliphatic hydrocarbon groups, halogen groups and aliphatic hydrocarbon groups substituted by a halogen group, or a salt thereof containing a physiolgically acceptable ion or ions, are of value in the treatment of patients having a toxic concentration of a metal, particularly iron, in the body whilst the iron complexes of such compounds are of value in the treatment of iron deficiency anaemia.

31 Claims, No Drawings

PHARMACEUTICAL COMPOSITIONS

This invention relates to compounds for use in medicine, particularly in the treatment of iron overload.

Certain pathological conditions such as thalassaemia, sickle cell anaemia, idiopathic haemochromatosis and aplastic anaemia are treated by regular blood transfusions. It is commonly found that such transfusions lead to a widespread iron overload, which condition can also arise through increased iron absorption by the body in certain other circumstances. Iron overload is most undesirable since, following saturation of the ferritin and transferrin in the body, deposition of iron can occur and many tissues can be adversely affected, particular toxic effects being degenerative changes in the myocardium, liver and endocrine organs. Such iron overload is most often treated by the use of desferrioxamine. However, this compound is an expensive natural product obtained by the culture of Streptomyces and, as it is susceptible to acid hydrolysis, it cannot be given orally to the patient and has to be given by a parenteral route. Since relatively large amounts of desferrioxamine may be required daily over an extended period, these disadvantages are particularly relevant and an extensive amount of research has been directed towards the development of alternative drugs. However, work has been concentrated on three major classes of iron chelating agents or siderophores, namely hydroxamates, ethylenediamine tetra-acetic acid (EDTA) analogues and catechols. The hydroxamates generally suffer from the same defects as desferrioxamine, being expensive and acid labile, whilst the other two classes are ineffective at removing iron from intracellular sites. Moreover, some cathechol derivatives are retained by the liver and spleen and EDTA analogues possess a high affinity for calcium and so are also likely to have associated toxicity problems.

We have accordingly studied the iron chelating ability of a wide range of compounds and have identified a group of compounds as being of particular use for the treatment of conditions involving iron overload. These compounds consist of a 1-hydroxypyrid-2-one in which one or more of the hydrogen atoms attached to ring carbon atoms are replaced by one of a carefully selected group of substituents. None of these compounds has previously been used therapeutically. Thus, although certain of the substituted compounds described herein have been suggested as potential anti-microbial agents, subsequent tests reported from the same source (Nishimura et al, Ann. Rept. Shionogi Res. Lab., 1966, 16, 37) showed the compounds to have negligible activity. In vitro tests illustrated the lack of anti-bacterial and anti-fungal activity and, although some compounds showed some anti-protozoal activity in vitro, when tested in mice against the fungus Trichomonas vaginalis all of the compounds tested proved to be inactive. Moreover, although it has been reported that 1-hydroxypyrid-2-one will form metal complexes, including an iron complex, it has never before been appreciated that certain substituted derivatives of this compound might be used with great advantage in a pharmaceutical context for the treatment of conditions producing toxic concentrations of iron in the body.

Accordingly the present invention comprises a compound being a 1-hydroxypyrid-2-one in which one or more of the hydrogen atoms attached to ring carbon atoms are replaced by a substituent selected from aliphatic acyl, aliphatic amide, aliphatic amine, carboxy, cyano, aliphatic ester, halogen, hydroxy and sulpho groups, alkoxy groups and alkoxy groups substituted by an alkoxy, aliphatic amide, aliphatic amine, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms in the compound is effected only by substituents selected from aliphatic hydrocarbon groups, halogen groups and aliphatic hydrocarbon groups substituted by a halogen group, or a salt thereof containing a physiologically acceptable ion or ions, for use in medicine.

Such compounds may be used in both human and veterinary treatment but are of particular interest for the treatment of the human body by therapy, especially in the context of the treatment of iron overload.

The 1-hydroxypyrid-2-ones are tautomeric compounds, being alternatively named as 2-hydroxypyridine 1-oxides, the two tautomeric structures being shown below for the unsubstituted parent compound.

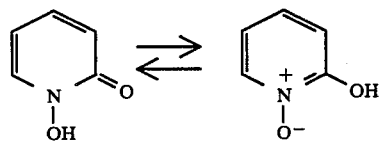

The ability of both the free compound and its iron complex to permeate membranes is important in the context of the treatment of iron overload, and it is also desirable for both to possess some degree of water solubility. A good indication of the physical properties of a compound and its iron complex in this respect is provided by the value of the partition coefficient (K part) obtained on partition between n-octanol and tris hydrochloride (20 mM, pH 7.4; tris representing 2-amino-2-hydroxymethylpropane 1,3-diol) at 20° C. and expressed as the ratio (concentration of compound in organic phase)/(concentration of compound in aqueous phase). Preferred compounds show a value of K part for the free compound of above 0.02 but less than 3.0, especially of above 0.2 but less than 1.0, together with a value of K part for the neutral 3:1 hydroxypyridone:iron-(III) complex of above 0.02 but less than 6.0, especially of above 0.2 but less than 1.0. The following comments upon preferences among the groups used for replacement of hydrogen atoms attached to carbon atoms of the pyridone ring are directed towards the use of compounds having partition coefficients in the free and complexed state which lie in these preferred ranges. For examples of measured partition coefficients of specific compounds reference should be made to Table 1 of Example 2.

More than one of the ring carbon atoms may be substituted, for example two of such atoms, either by the same substituent group or by different substituent groups, for example by halogen or especially by an aliphatic hydrocarbon group together with another type of substituent, although compounds in which only one of the ring carbon atoms is substituted are preferred. Substitution may occur at any of the 3-, 4-, 5-and 6-positions or at a combination of two or more of these positions. Particularly when the ring carbon atoms are substituted by the larger groups, however, there may be an advantage in avoiding substitution on a carbon alpha to the

system. The system is involved in the complexing with iron and the close proximity of one of the larger aliphatic hydrocarbon groups may lead to steric effects which inhibit complex formation. Substitution at the 5- and particularly the 4-position is thus of some especial interest.

Where a ring carbon atom is substituted by an aliphatic hydrocarbon group, this group may be cyclic or acyclic, having a branched chain or especially a straight chain in the latter case, and may be unsaturated or especially saturated. Groups of from 1 to 6 carbon atoms, particularly of 1 to 4 and especially of 1 to 3 carbon atoms, are of most interest. Alkyl groups are preferred, for example cyclic groups such as cyclopropyl and especially cyclohexyl but, more particularly preferred are acyclic groups such as isopropyl, n-propyl, ethyl and especially methyl. However, although substitution by an aliphatic hydrocarbon group, for example methyl, in addition to another substituent as specified above is quite acceptable, it will not generally contribute with any particular advantage to the properties of the compound and is thus not of especial interest.

In the case of substituted aliphatic hydrocarbon groups, the preferences as to the nature of these groups are broadly as expressed above with regard to the hydrocarbon group and hereinafter with regard to the substituent, for example these groups conveniently being substituted alkyl groups of 1 to 3 carbon atoms and particularly substituted methyl groups such as chloromethyl, ethoxymethyl, and especially hydroxymethyl. In general, however, substitutents as defined hereinbefore other than aliphatic hydrocarbon groups and substituted aliphatic hydrocarbon groups are of the most interest. Various preferences may be expressed among such other substituent groups, the following comments applying equally to these groups when substituted on the ring directly and, where appropriate, also to the groups when substituted on an aliphatic hydrocarbon or alkoxy group which is itself substituted on the ring.

An aliphatic acyl group may contain a sulphonyl or carbonyl group. The latter type are however preferred and although the acyl group may be a formyl group, alkylcarbonyl groups are of most interest. Such acyl groups may, for example, be of 2 to 4 or 5 carbon atoms, and particularly may contain alkyl groups of the type described above as being preferred as an aliphatic hydrocarbon group substituent on the ring, being, for example, —COCH$_2$CH$_3$ or especially —COCH$_3$. Alkoxy groups may conveniently be of 1 to 4 carbon atoms and contain similar alkyl groups to those which are preferred in the alkylcarbonyl groups, examples of such substituents being ethoxy and particularly methoxy. Alkoxy groups which are substituted, however, may often conveniently contain 2 or more carbon atoms in view of the relative instability of groups such as

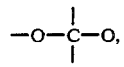

etc., so that a particular substituted alkoxy group of interest is —OCH$_2$CH$_2$OCH$_3$. Moreover, the presence of a hydrophilic substituent on an alkoxy group will tend to offset the hydrophobic effect of the aliphatic hydrocarbon group which that alkoxy group contains, thereby sometimes favouring the use of slightly larger alkoxy groups when these are substituted. Substituent alkoxy groups are of particular interest in the context of the present invention and are discussed in more detail hereinafter.

Amine substituents may consist of a group —NH$_2$ or its charged equivalent, a group —ṄH$_3$, which will be associated with a physiologically acceptable anion, for example a chloride or other halide ion, a solubilising ion such as that from methane sulphonic or isethionic acid, or an anion derived from the hydroxy group of the ring (OH→O$^-$), or such a —NH$_2$ or ṄH$_3$ group in which one or more of the hydrogen atoms is replaced by an aliphatic hydrocarbon group, for example such a group as is described above as a substitutent. Amide substituents may contain a sulphonyl or a carbonyl group. The latter type are, however, of most interest and the further discussion will therefore refer to them although it applies equally to the sulphonyl type. The amide substituent may be of the unsubstituted form —CONH$_2$, i.e. being a carbamoyl group, or may contain a nitrogen atom which is mono- or di-substituted as just described for the amine substituents, for example being a group —CONHCH$_3$, etc. Alternatively, the

grouping of the amide substituent may be arranged in the opposite sense so that the nitrogen atom of the amide grouping is attached to the ring, the carbonyl group being attached to an aliphatic hydrocarbon group, for example an alkyl group such as is described above as a substituent, or in the case of a carboxylic acid amide but not in that of a sulphonic acid amide, to hydrogen. In the case of an amide group arranged in this opposite sense, the nitrogen atom may carry a hydrogen atom or be mono-substituted as discussed for amide substituents of the first mentioned form, that form of amide substituent being the one of particular interest.

Carboxy and sulpho substituents, the former of which are preferred, may be present as the group —CO$_2$H or —SO$_3$H, or as the anion derived therefrom in combination with a physiologically acceptable cation, for example as described hereinafter. Ester substituents may contain a sulphonyloxy or preferably a carbonyloxy group and this may be arranged in either sense, i.e. with a carboxylic acid ester the group —CO.O— may have either the carbonyl group or the oxy group linked to the carbon atom of the ring (through an aliphatic hydrocarbon group on which the ester group is substituted, where appropriate). The other group of oxy and carbonyl will be linked to an aliphatic hydrocarbon group forming part of the ester group or, in the case where this is a carbonyl group may alternatively be linked to hydrogen (this latter possibility does not apply in the case of sulphonic acid esters). Once again, preferred aliphatic hydrocarbon groups contained by the ester group are those described above as substituents. Ester groups in which the oxy group is linked to the ring are preferred, for example the groups —O.COCH₃ and —O.COC₂H₅ rather than —CO₂CH₃ and —CO₂CH₂CH₃. With aliphatic hydrocarbon groups or alkoxy groups substituted by an ester group there is a particularly strong preference for the oxy group to be attached to this aliphatic hydrocarbon group or alkoxy group, groups such —CH₂O.COCH₃ therefore being of interest. Halogen substituents may conveniently be iodo, fluoro, bromo or especially chloro.

Among preferred substituents are the hydroxy group, and also alkoxy groups, for example ethoxy and particularly methoxy, and, more particularly, substituted alkoxy groups, especially those substituted by a hydroxy group or another alkoxy group, for example the substituted ethoxy groups such as —OCH₂CH₂OCOCH₃, —OCH₂CH₂NHCOCH₃, —OCH₂CH₂NH₂ and especially —OCH₂CH₂OH and —OCH₂CH₂OCH₃. Hydroxy substituted aliphatic hydrocarbon groups, for example hydroxymethyl, are also of generally greater interest than other substituted aliphatic hydrocarbon groups.

Although simple alkoxy substituents, the alkoxy groups of hydroxyalkoxy substituents and both components of alkoxyalkoxy substituents may, as indicated previously, be of a range of sizes, for example 1 to 6 carbon atoms, certain factors result in a preference for groups of a particular size. Thus, the hydrophilic/hydrophobic balance in a compound, which is indicated by its $K_{part}$ value, may be adjusted to a value in the preferred range quoted hereinbefore by the use of additional ring substituents, so that the hydrophobic effect of a large unsubstituted alkoxy group can be offset by the presence of a further hydrophilic substituent, such as a hydroxy group, on another carbon atom of the ring. However, it is generally preferable to use a single substituent which itself confers the appropriate degree of balance. Accordingly, unsubstituted alkoxy group substituents of 1 to 3 or 4, preferably 1 or 2 carbon atoms, and hydroxy substituted alkoxy group substituents of 2 to 4, preferably 2 or 3 carbon atoms (substituted methoxy groups being of less interest in view of the instability of the

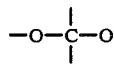

linkage referred to previously), are of particular interest. For similar reasons there is particular interest in alkoxy substituted alkoxy group substituents of 2 to 4, preferably 2 or 3 carbon atoms, in the first alkoxy group substituted onto the ring and of 1 to 4, preferably 1 to 3 carbon atoms in the second alkoxy group which is substituted onto the first alkoxy group, with the proviso that the overall number of carbon atoms is preferably no greater than 6, and especially no greater than 3 or 4 carbon atoms.

Although the hydroxy, methoxy, hydroxymethoxy and methoxyethoxy groups already referred to are of particular interest as substitutents, other specific examples of alkoxy and substituted alkoxy groups, in addition to those specifically mentioned previously, are 3-hydroxypropoxy, 2-hydroxy-1-methylethoxy and 3-methoxypropoxy.

Hydroxy, alkoxy, substituted alkoxy and other groups may conveniently be substituted at the 4-position of a 1-hydroxypyrid-2-one, for example at the 4-position of 1-hydroxy-6-methylpyrid-2-one or other C-methyl substituted 1-hydroxypyrid-2-one or, more especially, at the 4-position of otherwise unsubstituted 1-hydroxypyrid-2-one. Specific examples of compounds according to the present invention are thus as follows:

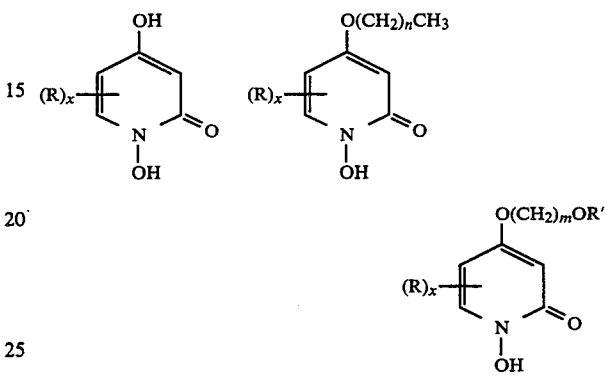

wherein R is a substituent group as defined hereinbefore, for example methyl and especially 6-methyl, hydroxy, etc., x is 0, 1, 2 or 3 (the ring not containing any further substituent R when x is 0), n is 0, 1, 2, 3 or 4, m is 1, 2, 3 or 4 and R' is hydrogen or —(CH₂)nCH₃, preferences among the groups at the 4-position being as described hereinbefore.

The compounds may, if desired, contain substituent groups, particularly an aliphatic amine, carboxy or sulpho group, in the salt form. Alternatively, a salt may be formed with the

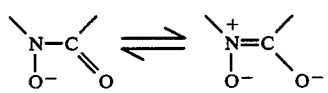

system produced by the loss of a proton from the hydroxy group N-substituted at the 1-position of the ring (or C-substituted at the 2-position of the ring in the tautomeric form). Such salts contain a physiologically acceptable cation, for example the cation of an alkali metal such as sodium, quaternary ammonium ions or protonated amines such as the cation derived from tris (tris represents 2-amino-2-hydroxymethyl propane 1,3-diol). Salt formation may be advantageous in increasing the water solubility of a compound but, in general, the use of the compounds themselves rather than their salts, is preferred.

Certain of the substituted 1-hydroxypyrid-2-ones described herein are known compounds, in particular the compounds having a single substituent at the 4-position which is an acetamido, amino, butoxy, carbamyl, carboxy, cyano, ethoxy, ethoxycarbonyl, methoxy or propoxy group, but all the other compounds described above are believed to be novel, including the particularly interesting compounds which are substituted by an additional hydroxy group, for example 1,4-dihydroxypyrid-2-one. The present invention thus includes, per se, the compounds described hereinbefore but excluding these known compounds.

The substituted 1-hydroxypyrid-2-ones (or 2-hydroxypyridine N-oxides) for use in the present invention may be synthesised by various routes applying standard reactions for the introduction of the substituent groups within the art of pyridine chemistry. In particular, substituents may be introduced either by replacement of a hydrogen atom or of an existing substituent at the appropriate position or positions in a pyridine or pyridine 1-oxide ring system. Pyridine compounds may conveniently be converted to the corresponding pyridine 1-oxide by the use of an oxidizing agent such as peracetic or perbenzoic acid. The oxygen atom at the 2-position of compounds according to the present invention may conveniently be introduced by the basic hydrolysis of a halogen group or the acidic hydrolysis of an alkoxy group, for example a methoxy group, at that position, preferably in a pyridine 1-oxide rather than a pyridine and conveniently following introduction of the other substituent groups or groups. Such a procedure will introduce a hydroxy group at the 2-position as in the 2-hydroxypyridine N-oxide tautomeric form shown hereinbefore.

Such procedures and the preparation of various suitable intermediates are described in the art, for example by Shaw et al, J. Amer. Chem. Soc., 1949, 71, 70 and ibid, 1950, 72, 4362, and particularly by Mizukami et al, Ann. Rept. Shionogi Res. Lab., 1966, 16, 29. A particularly useful type of intermediate for the preparation of the compounds described herein is a nitro substituted 2-chloro-pyridine N-oxide, 4-nitro, 5-nitro and 3,5-dinitro substituted compounds all being reported in the literature. Thus, 2-chloro-4-nitropyridine-1-oxide, for example, may be subjected to nucleophilic substitution to replace the nitro group by an alkoxy group or alkoxy substituted alkoxy group, for example $-OCH_3$ or $-OCH_2CH_2OCH_3$, the chloro group then being converted to a hydroxy group by basic hydrolysis. Alternatively, a nitro group substituent may be reduced to give an amino group which may in turn be acylated.

The compounds may be converted to salts formed with the anion produced by the loss of the hydroxy group proton or with a substituent such as a carboxy, sulpho or amino group by reaction with the appropriate base or acid according to standard procedures (amino substituted compounds of a zwitterion type containing a cation from the amino group and such a hydroxy group-derived anion may be prepared by crystallisation from aqueous media at a pH of about 9).

In general, it is preferred that the compounds are isolated in substantially pure form, i.e. substantially free from by-products of manufacture.

It will be appreciated that these are not the only routes available to these compounds and that various alternatives may be used as will be apparent to those skilled in the art, as will be the routes to the various intermediates required.

Moreover, it will be appreciated that certain of the compounds may be converted in vivo to other compounds which will be involved in the metal binding activity observed in vivo. This will be true, for example, of compounds containing ester groups which are likely to be converted to carboxy groups when the compounds are administered orally.

The compounds may be formulated for use as pharmaceuticals for veterinary, for example in an avian or particularly a mammalian context, or particularly human use by a variety of methods. For instance, they may be applied as an aqueous, oily or emulsified composition incorporating a liquid diluent which most usually will be employed for parenteral administration and therefore will be sterile and pyrogen free. However, it will be appreciated from the foregoing discussion in relation to desferrioxamine that oral administration is to be preferred and the compounds of the present invention may be given by such a route. Although compositions incorporating a liquid diluent may be used for oral administration, it is preferred to use compositions incorporating a solid carrier, for example a conventional solid carrier material such as starch, lactose, dextrin or magnesium stearate, the oral composition then conveniently being of a formed type, for example as tablets, capsules (including spansules), etc.

The present invention accordingly further comprises a pharmaceutical composition containing a compound being a a 1-hydroxypyrid-2-one in which one or more of the hydrogen atoms attached to ring carbon atoms are replaced by a substituent selected from aliphatic acyl, aliphatic amide, aliphatic amine, carboxy, cyano, aliphatic ester, halogen, hydroxy and sulpho groups, alkoxy groups and alkoxy groups substituted by an alkoxy, aliphatic amide, aliphatic amine, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms in the compound is effected only by substituents selected from aliphatic hydrocarbon groups, halogen groups and aliphatic hydrocarbon groups substituted by a halogen group, or a salt thereof formed between the anion produced by the loss of the hydroxy group proton and a physiologically acceptable cation, together with a physiologically acceptable solid carrier.

Other forms of administration than by injection or through the oral route may also be considered in both human and veterinary contexts, for example other forms known in the art such as the use of suppositories or pessaries, particularly for human administration.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition, it may be stated by way of guidance that satisfactory control of the amount of iron present in the human body will often be achieved using a daily dosage of about 0.1 g to 5 g, particularly of about 0.5 g to 2 g, veterinary doses being on a similar g/Kg body weight ratio. However, it will be appreciated that it may be appropriate under certain circumstances to give daily dosages either below or above these levels. Where desired, more than one compound according to the present invention may be administered in the pharmaceutical composition or, indeed, other active compounds may be included in the composition.

Although suggestions have previoulsy been made concerning use of certain of the compounds described herein in a pharmaceutical context as anti-microbials, these suggestions did not lead to a therapeutic use for the compounds. We have found that the 1-hydroxypyrid-2- ones described herein are particularly suited to the removal of iron from patients having an iron overload. The compounds form neutral 3:1 iron complexes at most physiological pH values, and have the advantage that they do not co-ordinate calcium or magnesium. Both the compounds and their complexes will partition into n-octanol indicating that they will permeate biological membranes, this property being confirmed in practice by tests of the ability of the $^{59}$Fe labelled iron complexes to permeate erythrocytes.

The 1-hydroxypyrid-2-ones possess a high affinity for iron(III), as evidenced by log $K_{sol}$ values (log $K_{sol}$ is defined as being equal to log $\beta_{Fe(L)n} + 21 - [pK_{sp} + n \log a_{L(H+)} + m \log a_L(Ca++)]$ where log $\beta_{Fe(L)n}$ is the cumulative affinity constant of the ligand in question for iron(III), $pK_{sp}$ is the negative logarithm of the solubility product for $Fe(OH)_3$ and has a value of 39, n and m are the number of hydrogen and calcium ions, respectively, which are bound to the ligand, and $a_{L(H+)}$ and $a_L(Ca++)$ are the affinities of the ligand for hydrogen ions and calcium ions, respectively). In order to solubilise iron(III) hydroxide, log $K_{sol}$ must be greater than 0 and in order to remove iron from transferrin, log $K_{sol}$ should be in excess of 6.0. The log $K_{sol}$ values for 1,4-dihydroxypyrid-2-one and 1-hydroxy-4-methoxypyrid-2-one by way of example, are 9.9 and 11.3, respectively, thus comparing favourably with those of the bidentate hydroxamates at about 4.0, of catechols at about 8.0, of desferrioxamine at 6.0, and of diethylenetriamine pentaacetic acid (DTPA) at 2.0. Moreover, the ability of the compounds to remove iron efficiently has been confirmed both by in vitro tests and also by in vivo tests in mice. It is particularly significant that these latter tests are successful whether the compound is given intraperitoneally or orally by stomach tube, the compounds generally either being stable under acidic conditions or being converted thereby to acid stable active compounds. Oral activity is not generally present among the other types of compound previously suggested for use as iron co-ordinating drugs and although certain EDTA analogues do show such activity, they possess drawbacks for pharmaceutical use.

In addition to the use described hereinbefore for the treatment of general iron overload, the hydroxypyridones described herein are also of interest for use in certain pathological conditions where there may be an excess of iron deposited at certain sites even though the patient does not exhibit a general iron overload, this being the case, for example, in certain arthritic and cancerous conditions. Indeed in some patients having such conditions, the patient may exhibit an overall aneamia and the metal-free 1-hydroxypyrid-2-ones may then be used in conjunction with an iron complex, for example an iron complex of the same or another of these 1-hydroxypyrid-2-ones, the iron complex acting to correct the overall anaemia whilst the metal-free compound acts to remove iron from pathological to physiological sites. Such iron complexes of the 1-hydroxypyrid-2-ones and their use in this context are discussed in detail hereinafter.

Uses of the compounds of the present invention for combination with metals other than iron may extend to the treatment of body fluids outside the body or even to quite other contexts than the treatment of patients. One particular area of some interest involves the treatment of patients on haemodialysis who may show a dangerous build up of aluminium in the body. For the treatment of such patients the compounds of the present invention may be insolubilised through attachment to a support material and then contacted with the patient's blood to remove aluminium therefrom. The support material may conveniently be one of various types of polymer described in the art for use in similar contexts, for example a carbohydrate material which may be of an agarose, dextran or other type, or a polystyrene or other material such as is used in ion-exchange resins.

Various approaches known in the art may be used for effecting attachment of the compounds to such support materials but one convenient approach is to use an acidic or basic group on the support material to provide an amide type linkage through reaction with the hydroxypyridone. Hydroxypyridones of particular interest in this context are those containing acidic or basic substituents on a ring carbon atom, i.e. those containing an aliphatic amine or a sulpho or especially a carboxy group substituent. (Substituted hydroxypyridones containing such a substituent which is an ionisable group are in fact generally of rather lesser interest for use in the pharmaceutical compositions of the present invention in view of their less effective membrane permeating properties.)

Just as iron overload can pose problems in some patients, iron deficiency anaemia can pose problems in others. As well as being of value as the metal-free compounds for the treatment of conditions involving iron overload, the substituted 1-hydroxypyrid-2-ones described hereinbefore are of interest in the iron complex form for the treatment of iron deficiency anaemia.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia, the level of iron uptake by the body from these compounds is often quite low, necessitating the administration of relatively high dosage levels of the compound. The administration of high dose, poorly absorbed, iron complexes may cause siderosis of the gut wall and a variety of side effects such as nausea, vomiting, constipation and heavy malodorous stools. We have now found that the iron complexes of the substituted 1-hydroxypyrid-2-ones described hereinbefore, none of which are believed to have been previously prepared, are of particular value in the treatment of such conditions.

Accordingly the present invention further comprises an iron complex of a 1-hydroxypyrid-2-one in which one or more of the hydrogen atoms attached to ring carbon atoms are replaced by a substituent selected from aliphatic acyl, aliphatic amide, aliphatic amine, carboxy, cyano, aliphatic ester, halogen, hydroxy and sulpho groups, alkoxy groups and alkoxy groups substituted by an alkoxy, aliphatic amide, aliphatic amine, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms in the compound is effected only by substituents selected from aliphatic hydrocarbon groups, halogen groups and aliphatic hydrocarbon groups substituted by a halogen group.

The comments made hereinbefore in relation to $K_{part}$ values for the metal-free compounds and their corresponding iron complexes in the case of preferred compounds apply equally to the selection of preferred metal-free compounds and of preferred iron complexes. The comments made hereinbefore with regard to preferences as to the nature and position of substituents thus apply equally in relation to the iron complexes.

The iron complexes present in the pharmaceutical compositions according to the present invention preferably contain iron in the ferric state. Although the use of complexes containing iron in the ferrous state may be considered, such complexes tend to be less stable and are thus of less interest. The iron complexes are preferably neutral, i.e. there being an internal balance of charges between the metal cation and the ligand(s) bound covalently thereto without the necessity for the presence of a non-covalently bound ion or ions, for example a chloride ion, to achieve balance. Moreover, the use of hydroxypyridones containing ionisable substituent groups is of less interest and it is preferred that this internal balance of charges is achieved by complexing with the iron cation the appropriate number of anions derived from a hydroxypyridone by the loss of a hydroxy proton which are necessary to produce neutrality. Preferred iron complexes of use in the present invention are thus of the 3:1 form, containing three hydroxypyridone anions complexed with a ferric cation. It will be appreciated, however, that the invention does not exclude the use of complexes of the 1:1 or particularly the 2:1 form, usually in association with a physiologically acceptable anion or anions to achieve neutrality, for example the chloride ion. It will be appreciated, therefore, that the invention particularly includes as compounds, per se, a neutral iron complex containing 1 molar proportion of iron(III) and 3 molar proportions of a hydroxypyridone as defined hereinbefore.

The iron complexes are conveniently prepared by the reaction of the hydroxypyridone and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol, chloroform and mixtures of these solvents together and/or with water where appropriate. In particular, methanol or especially ethanol may be used as the solvent where it is desired to effect the separation of at least a major part of a by-product such as sodium chloride by precipitation whilst the iron complex is retained in solution. Alternative procedures may, however, be used and will be apparent to those skilled in the art.

It will be appreciated that the nature of the iron complex obtained by the reaction of a hydroxypyridone and iron ions will depend both on the proportion of these two reactants and upon the pH of the reaction medium. Thus, for the preparation of the 3:1 ferric complex, for example, the hydroxypyridone and the ferric salt are conveniently mixed in solution in a 3:1 molar proportion and the pH adjusted to a value in the range of 6 to 9, for example 7 or 8. If a similar excess of hydroxypyridone:iron is employed, but no adjustment is made of the acidic pH which results on the admixture of the hydroxypyridone and an iron salt such as ferric chloride, then a mixture of the 2:1 and 1:1 complex will instead be obtained. Adjustment of the pH may conveniently be effected by the addition either of sodium carbonate or of a hydroxide base such as sodium or ammonium hydroxide, the use of a hydroxide base being or particular interest when preparing the iron complexes in batches of 20 g or more. When using a hydroxide base, the reaction may conveniently be carried out in a medium containing water as the solvent, for example in water or an ethanol:water mixture, and the pH adjusted by the addition of a 2 molar aqueous solution of the base. It will be appreciated that the presence of water in the reaction mixture will lead to the retention of a by-product in the iron complex on evaporation of the solvent (a chloride where the iron salt is ferric chloride). However, this can be removed, if desired, by procedures such as crystallisation from a suitable solvent system or sublimation in the particular case of ammonium chloride.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, be crystallised from a suitable solvent, for example water, an alcohol such as ethanol, or a solvent mixture, including mixtures containing an ether. The present invention thus further includes a process for the preparation of an iron complex of a 1-hydroxypyrid-2-one as defined hereinbefore which comprises reacting said hydroxypyridone with iron ions and isolating the resultant complex.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 3:1 [hydroxypyridone:iron(III)]-complex is of particular interest in a form free from by-products which are complexes containing different proportions of hydroxypyridone and iron, in particular the 2:1 and 1:1 complexes. Accordingly the present invention includes an iron complex, for example the 3:1 hydroxypyridone:iron(III) complex, of a 1-hydroxypyrid-2-one as defined hereinbefore, when in a form substantially free from iron complexes of the hydroxypyridone containing other proportions of iron. As indicated hereinafter, it may be advantageous under some circumstances for the iron complex to be used in admixture with the free hydroxypyridone and, if desired, such a mixture may be obtained directly by reacting a molar proportion of the hydroxypyridone and iron ions of greater than 3:1.

The iron complexes may be formulated as pharmaceuticals for veterinary, for example in an avian or particularly a mammalian context, or human use by a variety of methods and the invention includes a pharmaceutical composition comprising an iron complex as hereinbefore defined together with a physiologically acceptable diluent or carrier. The comments made hereinbefore with regard to the formulation of the metal-free compounds apply equally to the iron complexes, although in this instance compositions for parenteral administration are of greater interest particularly in the context of animal treatment. The problems of iron deficiency anaemia in newly born pigs arise primarily during the first three weeks or so of their life when a very rapid weight gain takes place. The iron complexes of the present invention may be used to treat piglets directly by a parenteral route, such as intramuscular or oral, for example as a liquid preparation "injected into the mouth". However, an alternative approach is to enhance the iron content of the milk on which the piglets are feeding by treating the mother pig using oral or parenteral administration, for example an injectable slow release preparation (such an approach may also be an interest in a human context). When it is applicable to feed piglets on foodstuffs other than the milk of the mother pig, it may also be possible to effect the pharmaceutical administration of the iron complex in this other foodstuff.

As with the metal-free compounds, the dosage of the hydroxypyridone iron complex which is given will depend on various factors, including the particular compound which is employed in the composition. It may be stated by way of guidance, however, that maintenance of the amount of iron present in the human body at a satisfactory level will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim.

Where desired, an iron complex of more than one hydroxypyridone as described above may be present in the pharmaceutical composition or indeed other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia in a pregnant female. It is believed, however, that the iron complexes of the present invnention have a further advantage in that they either do not have this effect or exhibit the effect at a lower level than the compounds at present used in the treatment of anaemia. Accordingly, it may often be the case that the level of zinc providing compound added to the composition may not require to be high or, with preferred formulations of the iron complexes, may be dispensed with altogether.

It has never before been appreciated that the iron complexes such as those described herein might be used, and with great advantage, in a pharmaceutical context. Accordingly the present invention includes an iron complex of a 1-hydroxypyrid-2-one as defined hereinbefore for use in medicine, particularly in the treatment of iron deficiency anaemia (in the broad sense of this term).

We have found that the iron complexes described herein are of value in the treatement of iron deficiency anaemia both in humans and also in a veterinary context, particularly for the treatment of various mammalian species and especially pigs. The complexes will partition into n-octanol indicating that they are able to permeate biological membranes, this property being confirmed in practice by tests of the ability of the $^{59}$Fe labelled iron complexes to permeate erythrocytes. The ability of the compounds in this respect will depend on the nature of the substituent(s) present therein and the reflection of this ability in the $K_{part}$ values of various compounds has been referred to hereinbefore.

The ability of the iron complexes of the present invention to promote iron uptake with a high level of efficiency, as compared with a range of other iron complexes currently marketed for the treatment of iron deficiency anaemia, has been confirmed by measurements in the rat small intestine. Once present in the bloodstream, the complexes will donate iron to transferrin, a position of equilibrium being set up between the complexes and transferrin. It is because of the existence of this equilibrium that the corresponding free hydroxypyridones may equally be used in the treatment of iron overload, although certain of these compounds may be of particular value for use in the free state for iron removal and others may be of particular value for use as iron complexes for iron supply.

Certain aspects of their formulation may enhance the activity of the complexes in particular contexts. Thus, although the neutral 3:1 ferric complexes are of particular value as being stable over a wide pH range from about 4 or 5 up to 10, they will dissociate at the pH values of less than 4 prevailing in the stomach to form a mixture of the 2:1 and 1:1 complex together with the free hydroxypyridone. If these complexes and the free hydroxypyridone are cleared simultaneously from the stomach, when they reach the small intestine a large proportion of the 3:1 complex should reform under the alkaline conditions present therein. However, in the event that this dissociation under acid conditions leads to a significant reduction in the uptake of iron by the body, due for instance to absorption of the free hydroxypyridone through the stomach wall, the uptake may be improved by using one or more of the following procedures in the formulation of the iron complex.

Firstly, one of several variations may be employed which avoid or reduce exposure of the iron complex to the acidic conditions of the stomach. Such approaches may involve various types of controlled release system, ranging from one, which may for example be based on a polymer, which simply provides a delayed release of the complex with time, through a system which is resistant to dissociation under acidic conditions, for example by the use of buffering, to a system which and is biased towards release under conditions such as prevail in the small intestine, for example a pH sensitive system which is stabilised towards a pH of 1 to 3 such as prevails in the stomach but not one of 7 to 9 such as prevails in the small intestine. Since the pH of the stomach is higher after a meal, it may be advantageous, whatever method of formulation is used, to administer the iron complexes at such a time.

A particularly convenient approach to a controlled release composition involves encapsulating the iron complex by a material which is resistant to dissociation in the stomach but which is adapted towards dissociation in the small intestine (or possibly, if the dissociation is slow, in the large intestine). Such encapsulation may be achieved with liposomes, phospholipids generally being resistant to dissociation under acidic conditions. The liposomally entrapped 3:1 iron(III) complexes can therefore survive the acid environment of the stomach without dissociating to the 2:1 and 1:1 complexes, and the free hydroxypyridone. On entry into the small intestine, the pancreatic enzymes rapidly destroy the phospholipid-dependent structure of the liposomes thereby releasing the 3:1 complex. Liposome disruption is further facilitated by the presence of bile salts. However, it is usually more convenient to effect the encapsulation, including microencapsulation, by the use of a solid composition of a pH sensitive nature.

The preparation of solid compositions adapted to resist dissociation under acidic conditions but adapted towards dissociation under non-acidic conditions is well known in the art and most often involves the use of enteric coating, whereby tablets, capsules, etc, or the inidividual particles or granules contained therein, are coated with a suitable material. Such procedures are described, for example, in the article entitled "Production of enteric coated capsules" by Jones in Manufacturing Chemist and Aerosol News, May 1970, and in such standard reference books as "Pharmaceutical Dosage Forms, Volume III by Liebermann and Lackmann (published by Marcel Decker). One particular method of encapsulation involves the use of gelatine capsules coated with a cellulose acetate phthalate/diethylphthalate layer. This coating protects the gelatin capsule from the action of water under the acid conditions of the stomach where the coating is protonated and therefore stable. The coating is however destabilised under the neutral/alkaline conditions of the intestine where it is not protonated, thereby allowing water to act on the gelatin. Once released in the intestine the rate of permeation of the intestine wall by the water soluble 3:1 iron-(III) complex is relatively constant irrespective of the position within the intestine, i.e. whether in the jejunum, ileum or large intestine. Other examples of methods of formulation which may be used include the use of polymeric hydrogel formulations which do not actually encapsulate the iron complex but which are resistant to dissociation under acidic conditions.

A second approach to countering the effect of the acidic conditions prevailing in the stomach is to formulate the iron complex in the pharmaceutical composition together with the metal-free hydroxypyridone from which it is derived. The dissociation of the neutral 3:1 ferric complex, for example, involves various equilibria between this complex, the 2:1 and 1:1 complexes, and the metal-free compound, so that the presence of the latter will inhibit this dissociation. Any proportion of the free compound can be advantageous in this context but little further advantage accrues from increasing the proportion beyond a certain level. A preferred range for the molar proportion of the free compound present in compositions according to the present invention is thus from 0 to 100 moles free hydroxypyridone:1 mole of iron complex, particularly the neutral 3:1 iron-(III) complex. Conveniently, a proportion of up to no more than 20, 30 or 50 moles:1 mole is used with a lower level of 0.5, 1 or 2 moles:1 mole. Although to obtain a marked effect upon dissociation of the iron complex a proportion of at least 5 or 10 moles:1 mole is usually employed it should be emphasised that even a molar ratio such as 1:1 will achieve a noticeable degree of acid stabilisation of the iron complex. Thus, although a range of, for example, from 10 moles:1 to 20 moles:1 mole of metal-free hydroxypyridone:iron complex will often be suitable to produce a marked effect, a range of, for example, 3 or even 1 mole:1 mole to 10 moles:1 mole will still produce a worthwhile effect without requiring administration of the larger amounts of the hydroxypyridone. The use of such a mixture is an important feature of the present invention since it can enable one to obtain almost quantitative uptake of iron from the complex. It should be appreciated, however, that the equilibrium between the complexes of various types and the metal-free compound will be effected by any take up of the latter in the body and the degree of such uptake from the stomach, for example, will depend on the particular metal-free compound.

A further advantage than prevention of dissociation of the iron complex under acidic conditions may accrue from the use of a free hydroxypyridone in admixture with its iron complex. Thus, as referred to hereinbefore, in certain pathological conditions there may be an excess of iron deposited at certain sites even though the patient exhibits an overall anaemia. In patients having such conditions the use of such a mixture has the advantage that the iron complex will remedy the overall anaemia whilst the free hydroxypyridone will act to remove iron from pathological to physiological sites. Moreover, there may be an advantage in formulating the iron complex of one hydroxypyridone as described herein with another one of such hydroxypyridones in free form or with a mixture of the corresponding free hydroxypyridone, present primarily to prevent dissociation of the iron complex, and of another such hydroxypyridone in free form, present primarily to effect iron transfer. Thus, it is preferable for the hydroxypyridone present in an iron donor to be rapidly metabolized so as to effect its removal from the system once it has given up its iron at an appropriate site in the system, whilst it is preferable for a hydroxypyridone being used as an iron remover not to be rapidly metabolized so that it remains in the system, taking up iron, for an extended period. For this reason the use of different hydroxypyridones in the free form and as the iron complex has certain advantages. Moreover, different hydroxypyridones may, for other reasons, function more efficiently either in the free form as an iron remover or in complex form as an iron donor. If desired, the free hydroxypyridone may alternatively be used in the form of a salt formed with the anion produced by the loss of a hydroxy proton and containing a physiologically acceptable cation, for example as described hereinbefore.

It will be appreciated that, as an alternative to combination with a different free hydroxypyridone of the same type, the iron complex may be used in combination with another iron chelating agent, for example an alternative form of hydroxypyridone such as is described in UK patent application Nos. 8308056, (published under the number GB 211876A (U.S. application Ser. No. 478,493, filed Mar. 24, 1983), and 8407181 (published under the number GB 2136807A (U.S. application Ser. No. 592,271, filed Mar. 22, 1984, now U.S. Pat. No. 4,585,780 issued Apr. 29, 1986).

When a free 1-hydroxypyrid-2-one is present in admixture with an iron complex of the same or a different 1-hydroxypyrid-2-one for the purpose of acting as an iron remover, then the amount of the metal-free compound may be different than when the free hydroxypyridone necessarily corresponds to that present in the iron complex and is present primarily to prevent dissociation. Thus the daily dosage of the iron complex may be as above and the daily dosage of the free hydroxypyridone may be that described in relation to the use of such compounds in iron overload conditions. Thus, it will be seen that the proportion of iron complex and free hydroxypyridone used in such a context may extend across a wide range but preferred amounts of the free compound tend to be higher than in the other instance involving the prevention of dissociation of the complex.

It will be appreciated that the present invention also includes a method for the treatment of a patient which comprises administering to said patient an amount of an iron complex of a 1-hydroxypyrid-2-one as described hereinbefore in order to effect an increase in the levels of iron in the patient's blood stream.

In addition to the pharmaceutical uses of the iron complexes discussed above they are also of potential interest as a source of iron in various other contexts including in cell and bacterial growth, in plant growth, as a colouring agent and in the control of iron transport across membranes.

This invention is illustrated by the following Examples.

EXAMPLES

EXAMPLE 1

The preparation of 1,4-dihydroxypyrid-2-one (1) 2-Chloro-4-nitropyridine-1-oxide 2-Chloro-pyridine-1-oxide (10 g) is cooled in an ice bath and treated with concentrated $H_2SO_4$ (15 ml), followed by the dropwise addition of a mixture of concentrated $H_2SO_4$ (15 ml) and fuming $HNO_3$ (27 ml, s.g. 1.5) over a 70 minute period. The acidic solution is heated in a steam bath for 2.5 hours, then allowed to reach room temperature and poured onto ice water (600 ml), stirring being continued until all the ice has melted. The resultant solid is filtered off and dissolved in hot chloroform, the solution being dried and the solvent evaporated in vacuo to give a yellow solid. The aqueous filtrate obtained after the removal of the original solid is neutralised with saturated aqueous $Na_2CO_3$ and extracted continuously with chloroform, the extract being dried and evaporated in vacuo to yield a yellow solid. The two yellow solids are combined and recrystallised from ethanol to give 2-chloro-4-nitro-pyridine-1-oxide as yellow crystals (7.46 g, 56%).

(2) 2,4-Dimethoxypyridine-1-oxide

Sodium methoxide is prepared by dissolving sodium metal (0.66 g) in methanol (33 ml). This solution is mixed with 2-chloro-4-nitro-pyridine-1-oxide (2.3 g) in methanol (20 ml) and the mixture is refluxed for 6 hours, then filtered and the solvent evaporated in vacuo. The resultant solid is extracted with chloroform, the chloroform solution then being reduced in volume and left to crystallise, yielding 2,4-dimethoxypyridine-1-oxide in 54% yield.

(3) 1,4-Dihydroxypyrid-2-one 2,4-Dimethoxypyrid-1-oxide is refluxed together with 20% w/v HCl for 13 hours. On cooling the solution 2,4-dihydroxypyridine-1-oxide is obtained as an orange-white solid (0.42 g, 30%), $\delta(d_6DMSO + $ trace of $D_2O)$, 6.08 (s, 1H), 6.12 (q, 1H), 7.88 (d, 1H).

EXAMPLE 2

The preparation of 1-hydroxy-4-methoxypyrid-2-one (1) 2-Chloro-4-methoxypyridine-1-oxide Sodium (0.46 g) is dissolved in absolute methanol (50 ml) and the resultant solution of sodium methoxide is added to a solution of 2-chloro-4-nitropyridine-1-oxide (3.5 g, prepared as described in Example 1) in methanol (10 ml). The reaction mixture is allowed to stand at room temperature for 50 hours and is then subjected to rotary evaporation to give 2-chloro-4-methoxypyridine-1-oxide.

(2) 1-Hydroxy-4-methoxypyrid-2-one

2-Chloro-4-methoxypyridine-1-oxide (3.3 g) is dissolved in 10% w/v aqueous NaOH (33 ml) and the mixture is heated on a steam bath for 3.5 hours when it is cooled and acidified with concentrated HCl to a pH of 2.5 to yield white crystals. Recrystallisation of these from water gives 1-hydroxy-4-methoxypyrid-2-one (0.75 g, 20%), m.p. 174°–175° C., $\delta(D_2O)$ 5.9 (s, 1H), 6.00 (q, 1H), 7.5 (d, 1H).

EXAMPLE 3

Preparation of 1-hydroxy-4-(2'-methoxyethoxy)-pyrid-2-one (1) 2-Chloro-4-(2'-methoxyethoxy)-pyridine-1-oxide Sodium metal (0.23 g) is dissolved in redistilled methoxyethanol (30 ml). The resulting solution is added to 2-chloro-4-nitro-pyridine-1-oxide (1.75 g, prepared as described in Example 1) and stirred for 28 hours at 20° C. The methoxy-ethanol is removed by distillation under reduced pressure leaving an oily brown solid which is washed with diethyl either (25 ml) and then dissolved in water (25 ml). The aqueous solution is extracted into chloroform (3×25 ml) and the extracts are then evaporated in vacuo to give 2-chloro-4-(2'-methoxyethoxy)-pyridine-1-oxide as a yellow solid.

(2) 1-Hydroxy-4-(2'-methoxyethoxy)-pyrid-2-one

2-Chloro-4-(2'-methoxyethoxy)-pyridine-1-oxide is treated with 10% w/v aqueous NaOH and the mixture is heated on a steam bath for 3 hours. The resulting solution is acidified to pH 2 with concentrated HCl, then reduced in volume by evaporating in vacuo and left to crystallise. The resultant white solid is recrystallised from ethanol to give 1-hydroxy-4-(2'-methoxyethoxy)-pyrid-2-one (0.58 g, 29%), m.p. 134° C., $\delta(CDCl_3)$ 3.42 (s, 3H), 3.7 (t, 1H), 4.08 (t, 1H), 6.05 (d, 1H), 6.05 (q, 1H), 7.62 (t, 1H).

EXAMPLE 4

Partition data on 1-hydroxypyrid-2-ones and their iron complexes

The partition coefficient K part, being the ratio (concentration of compound in n-octanol)/(concentration of compound in aqueous phase) on partition between n-octanol and aqueous tris hydrochloride (20 mM, pH 7.4), is measured at 20° C. the compounds of Examples 1 to 3 and 1-hydroxypyrid-2-one by way of comparison, and for their iron complexes (at $10^{-4}M$) by spectrophotometry. Acid washed glassware is used throughout and, following mixing of 5 ml of the $10^{-4}M$ aqueous solution with 5 ml n-octanol for 1 minute, the aqueous n-octanol mixture is centrifuged at 1,000 g for 30 seconds. The two resulting phases are separated for a concentration determination by spectrophotometry on each. For the free hydroxypyridones, the range 220–340 nm is used for concentration determinations whilst for the iron complexes, the range 340–640 nm is used.

Values typical of those obtained are shown in Table 1.

TABLE 1

| | Partition coefficients | |
|---|---|---|
| | Partition coefficient $K_{part}$ | |
| Compound | Free Compound | Iron complex $[Fe^{III}$—(compound)$_3]$ |
| 1-hydroxypyrid-2-one | 0.3 | 0.95 |
| 1,4-dihydroxypyrid-2-one | 0.04 | 0.04 |
| 1-hydroxy-4-methoxypyrid-2-one | 0.15 | 4.85 |
| 1-hydroxy-4-(2'-methoxyethoxy)-pyrid-2-one | 0.14 | 0.6 |

EXAMPLE 5

In vitro tests of iron binding capacity

The 1-hydroxypyrid-2-ones used in this Example were prepared as described in Examples 1, 2 and 3, and 1-hydroxypyrid-2-one was also used for comparative purposes.

(1) Mobilisation of iron from ferritin

Horse spleen ferritin (Sigma) was used without further purification and its iron content was estimated spectrophotometrically at 420 nm. The ferritin solution in phosphate buffered saline (Dulbecco-OXOID, $10^{-6}$ M, pH 7.4) was enclosed in a Visking dialysis tube and dialysed against a $3 \times 10^{-3}$ M buffered solution of one of various pyridones as indicated in Table 2. The absorption spectrum of the resulting iron(III) complex in the dialysis solution was recorded after 6 and 24 hours. For comparative purposes, the procedure was repeated using a blank control.

The results are shown in Table 2 where the percentage of ferritin-bound iron removed by the compound under test is shown. For comparative purposes, results reported in the literature for similar tests with $1 \times 10^{-3}$ M desferrioxamine (Crichton et al, J. Inorganic Biochem., 1980, 13, 305) and with $6 \times 10^{-3}$ M LICAMS (Tufano et al, Biochem. Biophys. Acta, 1981, 668, 420) are also given in the Table. It will be seen that the pyridone compounds are able to remove iron effectively from ferritin in contrast with desferrioxamine and LICAMS (although the latter will remove iron in the presence of ascorbic acid such a mixture is very difficult to manage clinically). These results shown in Table 2 may be confirmed by separating apoferritin (in admixture with ferritin) and the particular hydroxypyridone iron(III) complex from the reaction product in each case by chromatography on Sephadex G10.

TABLE 2

| | Removal of iron from ferritin | |
|---|---|---|
| | Percentage of iron removed | |
| Compound | 6 hours | 24 hours |
| Control | 0 | 0 |
| 1-hydroxypyrid-2-one | 34[1] | — |
| 1,4-dihydroxypyrid-2-one | 22 | 54 |
| 1-hydroxy-2-methoxypyrid-2-one | 13 | 46 |
| 1-hydroxy-4-(2'-methoxyethoxy)-pyrid-2-one | 2 | 8 |
| Desferrioxamine (1 mM) | 1.5 | — |
| LICAMS (6 mM + 12 mM ascorbic acid) | 7 | — |

TABLE 2-continued

| | Removal of iron from ferritin | |
|---|---|---|
| | Percentage of iron removed | |
| Compound | 6 hours | 24 hours |

[1]1-hydroxypyrid-2-one iron complex precipitated from incubation medium.

(2) Mobilisation of iron from transferrin

Human transferrin (Sigma) was loaded with iron(III) by the method of Bates and Schlaback, J. Biol. Chem. (1973) 248, 3228. $^{59}$Iron(III) transferrin ($10^{-5}$ M) was incubated with a $4 \times 10^{-3}$ M solution in tris HCl (0.1 M, pH 7.4) of one of various pyridones as indicated in Table 3 for periods of 6 hours and 24 hours. The solution was then dialysed against phosphate buffered saline for 24 hours. The $^{59}$Fe remaining in the dialysis tube was then recorded. For comparative purposes, this procedure was repeated with desferrioxamine and EDTA.

The results are shown in Table 3 in terms of the percentage of transferrin bound iron removed by the compound under test. illustrate the efficiency of the compounds at iron removal. The results shown in Table 3 may be confirmed by separating apotransferrin (in admixture with transferrin) and the particular hydroxypyridone iron complex from the reaction product in each case by chromatography on Sephadex G10.

TABLE 3

| | Removal of iron from transferrin | |
|---|---|---|
| | Percentage of iron removed | |
| Compound | 6 hours | 24 hours |
| 1-hydroxypyrid-2-one | 60 | 73 |
| 1,4-dihydroxypyrid-2-one | 80 | 91 |
| 1-hydroxy-4-methoxypyrid-2-one | 70 | 71 |
| 1-hydroxy-4-(2'-methoxyethoxy)-pyrid-2-one | 72 | 75 |
| Desferrioxamine | 17 | 22 |
| EDTA | 27 | 67 |

EXAMPLE 6

In vivo tests of iron binding capacity

The 1-hydroxypyrid-2-one used in this Example was prepared as described in Example 1.

Mice were injected intraperitoneally with iron dextran (2 mg) at weekly intervals over a four week period. Two weeks after the final injection, the mice were injected via the tail vein with $^{59}$Fe lactoferrin (human lactoferrin, 1 mg per injection 2 μCi). The mice were then caged individually. After a ten day period, 1,4-hydroxypyrid-2-one was administered to groups of 8 mice at 10 mg per mouse either intraperitoneally or intragastrically (in each case 3 of the mice received only one dose whilst 5 received 2 doses at a 24 hour interval). The excretion of iron was recorded at either 12 or 24 hourly intervals over a three day period before and a two day period after administration of the compound. For comparative purposes, the procedure was repeated with a blank control and with desferrioxamine, also at 10 mg per mouse (the intraperitoneally treated mice receving one dose of desferrioxamine and the intragastrically treated mice two doses at a 24 hour interval).

The results are shown in Table 4, being given on the basis of the control representing 100% excretion, and illustrate the particular advantage of the pyridones as compared with desferrioxamine for oral administration. It should be mentioned that the large standard deviation (SD) values are somewhat misleading as uniformly positive results can yield high SDs which might be taken to suggest that the results are not significantly different from zero. However, this is not the case here, the large SD values being a consequence of the large range among the positive responses.

TABLE 4

| | Excretion of iron in vivo | | | |
|---|---|---|---|---|
| | Intraperitoneal Administration | | Intragastric Administration | |
| Compound | Number of Mice | Excretion of $^{59}$Fe ± SD percent | Number of Mice | Excretion of $^{59}$Fe ± SD percent |
| Control | 12 | 100 ± 10 | — | — |
| 1,4-dihydroxy-pyrid-2-one | 11 | 195 ± 57 | 6 | 166 ± 40 |

EXAMPLE 7

Preparation of iron complexes

The iron complex of 1-hydroxy-4-methoxypyrid-2-one is prepared by either procedure (a) or procedure (b). (a) An aqueous solution of ferric chloride is reacted for 5 minutes at room temperature with an aqueous solution containing 3 molar equivalents[(1)] of 1-hydroxy-4-methoxypyrid-2-one. The resultant solution is adjusted to pH 7.0 using 2 molar aqueous sodium hydroxide and is then freeze dried. The resulting powder is extracted with chloroform, filtered and the filtrate subjected to rotary evaporation to give an essentially quantitative yield of the neutral complex containing the 1-hydroxy-4-methoxypyrid-2-one anion and the ferric cation in 3:1 proportion. Recrystallisation of the 3:1 complex from ethanol gives orange crystals, m.p. 103°–106° C.

[(1)]The concentration of the hydroxypyridone is 0.1 M although this figure may be varied, for example in a range of 0.01 to 0.5 M, being constrained at the upper end of the range by the solubility of the compound in the reactions solvent.

(b) An ethanolic solution of ferric chloride is reacted for 5 minutes at room temperature with a chloroform solution containing 3 molar equivalents of 1-hydroxy-4-methoxypyrid-2-one. The resultant solution is neutralised by the addition of solid sodium carbonate, the precipitated sodium chloride removed by filtration and the filtrate evaporated to give an essentially quantitative yield of the 3:1 complex, m.p. 103°–106° C.

The 3:1 iron(III) complexes of 1,4-dihydroxypyrid-2-one and 1-hydroxy-4-(2'-methoxyethoxy)-pyrid-2-one may be prepared in an exactly similar manner.

When an excess (5 to 50 molar equivalents) of any pyridone is used, both procedure (a) and procedure (b) lead to an essentially quantitative yield of the excess pyridone in free form in admixture with the 3:1 complex.

EXAMPLE 8

The ability of iron complexes to donate iron to apotransferrin

Apotransferrin ($10^{-4}$ M) and the iron complex of 1-hydroxy-4-methoxypyrid-4-one ($10^{-4}$ M; prepared as described in Example 7) were incubated together in tris hydrochloride (50 mM, buffered to pH 7.4) at 37° C. for 10 minutes when a 1 ml aliquot was removed from the medium and added to a PD10 colum. 0.5 ml fractions were collected directly into scintillation vials for counting. The $^{59}$Fe associated with both the apotransferrin and the ligand was estimated and it was found that over 90% of the iron was removed from the iron complex.

EXAMPLE 9

In vitro tests on permeation of rat jejunal sac by iron complexes

The iron uptake into the serosal space of the inverted rat jejunal sac was compared for various iron compounds. Rats (male Sprague Dawley, 60 g) were killed and the jejunum removed, everted and cut into three segments (4 cm length). The segments were tied at both ends and filled with Krebs Ringer buffer (0.2 ml) and incubated in Krebs Ringer buffer containing $^{59}$Fe complexes at 37° C. for periods up to 1 hour. The contents of the sac were counted for $^{59}$Fe and measured spectrophotometrically.

The results obtained for the three iron complexes described in Example 7 and for seven other iron compounds which are each contained in preparations marketed for the treatment of iron deficiency anaemia are shown in Table 5, the iron uptake for each compound being shown relative to that for ferric chloride as 1. It will be seen that the complexes of Example 7 each provide a level of iron uptake which is significantly higher than the levels observed for any of the 7 compounds in current use for the treatment or iron deficiency anaemia.

TABLE 5

| Compound | Relative Iron Uptake | Compound | Relative Iron Uptake |
|---|---|---|---|
| FeCl$_3$ | 1 | FeCl$_3$ | 1 |
| Fe$^{III}$ complex of: | | Fe$^{II}$ sulphate | 2.4 |
| 1,4-dihydroxypyrid-2-one | 9.4 | Fe$^{II}$ fumarate | 4.0 |
| 1-hydroxy-4-methoxy-pyrid-2-one | 12.3 | Fe$^{II}$ gluconate | 1.6 |
| 1-hydroxy-4-(2'-methoxyethoxy)-pyrid-2-one | 11.4 | Fe$^{II}$ succinate | 2.0 |
| | | Fe$^{III}$ EDTA | 3.6 |
| | | Fe$^{III}$ ascorbate | 0.4 |
| | | Fe$^{III}$ citrate | 2.0 |

We claim:

1. A method for the treatment of a patient having a toxic concentration of iron in the body which comprises administering to said patient a compound being a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy groups and alkoxy groups substituted by an alkoxy, aliphatic amide, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group, or a salt therof containing a physiologically acceptable cation in an amount effective to reduce said toxic concentration of the metal.

2. The method according to claim 1, in which at least one of the ring carbon atom substituents is a hydroxy, alkoxy or substituted alkoxy group, or a hydroxy- or alkoxy-substituted aliphatic hydrocarbon group.

3. The method according to claim 2, in which at least one of the ring carbon atom substituents is a hydroxy group, an alkoxy group of 1 to 5 carbon atoms, an alkoxy group of 2 to 4 carbon atoms substituted by a hydroxy group, or an alkoxy group of 2 to 4 carbon atoms substituted by an alkoxy group of 1 to 4 carbon atoms, the total number of carbon atoms in the alkoxyalkoxy group being 3 to 6.

4. The method according to claim 3, in which the ring carbon atoms of the 1-hydroxypyrid-2-one are substituted by a single one of said substituents and additionally by one or more aliphatic hydrocarbon groups of 1 to 4 carbon atoms.

5. The method according to claim 3, in which the ring carbon atoms of the 1-hydroxypyrid-2-one are substituted only by a single one of said substituents.

6. The method according to claim 5, in which the single one of said substituents is located at the 4-position of the 1-hydroxypyrid-2-one.

7. The method according to claim 1, in which the 1-hydroxypyrid-2-one is 1-hydroxy-4-methoxypyrid-2-one, 4-ethoxy-1-hydroxypyrid-2-one, 1,4-dihydroxypyrid-2-one, 1-hydroxy-4-(2'-hydroxyethoxy)-pyrid-2-one, 1-hydroxy-4-(3'-hydroxypropoxy)-pyrid-2-one or 1-hydroxy-4-(2'-methoxyethoxy)-pyrid-2-one.

8. The method according to claim 1, wherein said at least one substituent is an alkoxy group substituted by an alkoxy, aliphatic amide, aliphatic ester, halogen or hydroxy group, and wherein at least one additional hydrogen atom may be substituted by a hydroxy group.

9. The method of claim 8, wherein one of the said hydrogen atoms attached to the ring carbon atoms of the 1-hydroxypyrid-2-one is replaced by a $C_{2-4}$ alkoxy group substituted by a hydroxy group or by a $C_{1-4}$ alkoxy group, with the total number of carbon atoms in the alkoxyalkoxy group ranging from 3 to 6, and wherein at least one more of the said hydrogen atoms can be replaced by an aliphatic group of 1 to 4 carbon atoms.

10. A method for the treatment of a patient to effect an increase in the level of iron in the patient's bloodstream which comprises adminstering to said patient a compound being an iron complex of a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy groups and alkoxy groups substituted by an alkoxy, aliphatic amide, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group, in an amount effective to achieve such an increase.

11. The method according to claim 10, in which at least one of the ring carbon atom substituents is a hydroxy, alkoxy or substituted alkoxy, group, or a hydroxy- or alkoxy-substituted aliphatic hydrocarbon group.

12. The method according to claim 11, in which at least one of the ring carbon atom substituents is a hydroxy group, an alkoxy group of 1 to 5 carbon atoms, an alkoxy group of 2 to 4 carbon atoms substituted by a hydroxy group, or an alkoxy group of 2 to 4 carbon atoms substituted by an alkoxy group of 1 to 4 carbon atoms, the total number of carbon atoms in the alkoxyalkoxy group being 3 to 6.

13. The method according to claim 12, in which the ring carbon atoms of the 1-hydroxypyrid-2-one are substituted by a single one of said substituents and additionally by one or more aliphatic hydrocarbon groups of 1 to 4 carbon atoms.

14. The method according to claim 12, in which the ring carbon atoms of the 1-hydroxypyrid-2-one are substituted only by a single one of said substituents.

15. The method according to claim 14 in which the single one of said substituents is located at the 4-position of the 1-hydroxypyrid-2-one.

16. The method according to claim 10, in which the 1-hydroxypyrid-2-one is 1-hydroxy-4-methoxypyrid-2-one, 4-ethoxy-1-hydroxypyrid-2-one, 1,4-dihydroxypyrid-2-one, 1-hydroxy-4-(2'-hydroxyethoxy)-pyrid-2-one, 1-hydroxy-4-(3'-hydroxypropoxy)-pyrid-2-one or 1-hydroxy-4-(2'-methoxyethoxy)-pyrid-2-one.

17. The method according to claim 16, in which the iron complex is the neutral 3:1 1-hydroxypyrid-2-one:iron(III) complex.

18. The method according to claim 10, in which the iron complex is the neutral 3:1 1-hydroxypyrid-2-one:iron(III) complex.

19. A pharmaceutical composition comprising a neutral 3:1 1-hydroxypyrid-2-one:iron(III) complex of a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy groups and alkoxy groups substituted by an alkoxy, aliphatic amide, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group, together with a physiologically acceptable diluent or carrier.

20. The pharmaceutical composition according to claim 19, which comprises a sterile, pyrogen-free diluent.

21. The pharmaceutical composition according to claim 19 which comprises a solid carrier.

22. The pharmaceutical composition according to claim 21 which is adapted to release of the iron complex in the intestine rather than in the stomach.

23. The pharmaceutical composition according to claim 19 in unit dosage form.

24. The pharmaceutical composition according to claim 19, in which at least one of the ring carbon atom substituents is a hydroxy group, an alkoxy group of 1 to 5 carbon atoms, an alkoxy group of 2 to 4 carbon atoms substituted by a hydroxy group, or an alkoxy group of 2 to 4 carbon atoms substituted by an alkoxy group of 1 to 4 carbon atoms, the total number of carbon atoms in the alkoxyalkoxy group being 3 to 6.

25. A compound being a neutral 3:1 1-hydroxypyrid-2-one:iron (III) complex of a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy groups and alkoxy groups substituted by an alkoxy, aliphatic amide, aliphatic ester, halogen or hydroxy group, aliphatic hydrocarbon groups and aliphatic hydrocarbon groups substituted by an alkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group.

26. The compound according to claim 25, in which at least one of the ring carbon atom substituents is a hydroxy, alkoxy, substituted alkoxy, or hydroxy- or alkoxy-substituted aliphatic hydrocarbon group.

27. The compound according to claim 26, in which at least one of the ring carbon atom substituents is a hydroxy group, an alkoxy group of 1 to 5 carbon atoms, an alkoxy group of 2 to 4 carbon atoms substituted by a hydroxy group, or an alkoxy group of 2 to 4 carbon atoms substituted by an alkoxy group of 1 to 4 carbon atoms, the total number of carbon atoms in the alkoxyalkoxy group being 3 to 6.

28. The compound according to claim 27, in which the ring carbon atoms of the 1-hydroxypyrid-2-one are substituted by a single one of said substituents and additionally by one or more aliphatic hydrocarbon groups of 1 to 6 carbon atoms.

29. The compound according to claim 27, in which the ring carbon atoms of the 1-hydroxypyrid-2-one are substituted only by a single one of said substituents.

30. The compound according to claim 29, in which the single one of said substituents is located at the 4-position of the 1-hydroxypyrid-2-one.

31. The compound according to claim 30, in which the 1-hydroxypyrid-2-one is 1-hydroxy-4-methoxypyrid-2-one, 4-ethoxy-1-hydroxy-pyrid-2-one, 1,4-dihydroxypyrid-2-one, 1-hydroxy-4-(2'-hydroxyethoxy)-pyrid-2-one, 1-hydroxy-4-(3'-hydroxypropoxy)-pyrid-2-one or 1-hydroxy-4-(2'-methoxyethoxy)-pyrid-2-one.

* * * * *